United States Patent [19]
Wolf et al.

[11] Patent Number: 5,498,704
[45] Date of Patent: Mar. 12, 1996

[54] PREPARATION OF ALKYL GLYCOSIDES

[75] Inventors: Gerhard Wolf, Mannheim; Alfred Oftring, Bad Duerkheim; Guenter Oetter, Frankenthal; Richard R. Schmidt; Wolfgang Klotz, both of Konstanz, all of Germany

[73] Assignee: BASF Aktiengesellschaft, Ludwigshafen, Germany

[21] Appl. No.: 302,779

[22] PCT Filed: Apr. 8, 1993

[86] PCT No.: PCT/EP93/00875

§ 371 Date: Sep. 21, 1994

§ 102(e) Date: Sep. 21, 1994

[87] PCT Pub. No.: WO93/21197

PCT Pub. Date: Oct. 28, 1993

[30] Foreign Application Priority Data

Apr. 21, 1992 [DE] Germany .......................... 42 13 016.6

[51] Int. Cl.⁶ .................................................. C07H 17/00
[52] U.S. Cl. ............................................................ 536/18.6
[58] Field of Search ............................................. 536/18.6

[56] References Cited

U.S. PATENT DOCUMENTS

| | | |
|---|---|---|
| 3,547,828 | 12/1970 | Mansfield et al. . |
| 3,598,865 | 8/1971 | Lew . |
| 3,839,318 | 10/1974 | Mansfield . |

FOREIGN PATENT DOCUMENTS

| | | |
|---|---|---|
| 252241 | 7/1987 | European Pat. Off. . |
| 364852 | 4/1990 | European Pat. Off. . |
| 0362671 | 4/1990 | European Pat. Off. . |
| 1183894 | 12/1964 | Germany . |

OTHER PUBLICATIONS

Angew. Chem. Int. Ed. Engl., vol. 25, pp. 212–235, 1986, Richard R. Schmidt, "New Methods for the Synthesis of Glycosides and Oligosaccharides–Are There Alternatives to the Koenigs–Knorr Method?".

Pure & Appl. Chem., vol. 63, No. 4, pp. 519–528, 1991, Pierre Sinay, "Recent Advances in Glycosylation Reactions".

Carbohydrate Research, vol. 12, pp. 421–428, 1970, David M. Hall, et al., "4,6–O–Alkylidene Derivatives of D–Glucose and its Methyl Pyranosides. An Improved Acetalation Procedure".

Houben–Weyl, vol. 6/3, pp. 33–36, 1965.

*Primary Examiner*—John W. Rollins
*Attorney, Agent, or Firm*—Oblon, Spivak, McClelland, Maier & Neustadt

[57] ABSTRACT

A process is described for preparing alkyl glycosides by reacting reducing saccharides with dialkyl sulfate whose alkyl groups contain at least 6 carbon atoms, in a molar ratio of saccharides to dialkyl sulfate of 1:1 to 1:5, the reaction mixtures, which contain alkyl monoglycosides and alcohol sulfates as essential constituents, being used as surfactants, preferably in detergents and cleaning agents.

16 Claims, No Drawings

PREPARATION OF ALKYL GLYCOSIDES

The invention relates to the preparation of alkyl glycosides by alkylation of reducing saccharides by means of dialkyl sulfates in the presence of a base and a solvent.

Surface-active compounds based on renewable raw materials are becoming increasingly important. In this connection fatty alcohol sulfates and methyl esters of α-sulfofatty acids may be mentioned as examples of anionic surfactants, while carbohydrate fatty acid esters, fatty alkyl glucamides and, in particular, alkyl glycosides may be mentioned as examples of nonionic surfactants. Alkyl glycosides have been known for a long time as carbohydrate surfactants, but on account of their relatively complicated preparation have hitherto been used only to a limited extent in detergents and cleaning agents. Alkyl glycosides may be prepared from the corresponding halides and long-chain alcohols by the conventional Königs-Knorr method via activation of the C-1 position. A whole range of further, generally complicated glycosylation variants are described in the literature, cf. P. Sinay, Pure & Appl. Chem., Vol. 63 (1991), 519 and R. R. Schmidt, Angew. Chem. Vol. 98 (1986), 213.

Alkyl glycosides are in principle prepared industrially by two different methods. In the transacetalation method, a hydrophilic monosaccharide unit is reacted in a first process stage with a short-chain alcohol (generally n-butanol or glycol) under acid catalysis to form a short-chain alkyl glycoside, which is then converted to the surface-active alkyl glycoside in a second stage by reaction with a long-chain alcohol (transacetalation). In another common method a monosaccharide unit is reacted directly with the long-chain, hydrophobic alcohol under acid catalysis. Many variants of the two preparation methods are described in the patent literature, e.g. in U.S. Pat. No. 3,547,828, U.S. Pat. NO. 3,598,865, U.S. Pat. No. 3,839,318, EP-A-0 362 671 and EP-A-0 252 241.

Since both aforedescribed glycosylation processes involve an equilibrium reaction, the alcohol component is in each case used in excess, and the excess alcohol has to be removed from the reaction product after the reaction. The distillative separation of long-chain alcohols from the reaction mixture is technically complicated and expensive. Moreover, on account of the thermal instability of the alkyl glycosides, the reaction product is seriously discolored. The alkyl glycosides obtainable in this way are mixtures of alkyl monoglycosides and alkyl oligoglycosides and polyglycosides.

It is known from U.S. Pat. No. 4,663,444 that glycosides which are alkylated or arylated in the C-6 position can be prepared by reacting 1-alkyl glycosides with methyl mesylates of the formula R'—O—SO$_2$CH$_3$ (R'=aryl, aralkyl, alkyl or alkenyl of 1 to 20 carbon atoms) in the presence of bases such as KOH and of solvents such as dimethyl sulfoxide.

The peralkylation of carbohydrates by means of dimethyl sulfate has been known for a long time, cf. Houben-Weyl, Vol. 6/3, 35f (1965). Also, the selective methylation of glucose in the C-1 position by means of dimethyl sulfate is described in the literature, cf. D. M. Hall and O. A. Stamm, Carbohydr. Res., Vol. 12 (1970), 412.

It is an object of the present invention to provide an improved process for preparing alkyl glycosides that are suitable for use in detergents.

We have found that this object is achieved by a process for preparing alkyl glycosides by alkylation of reducing saccharides in the presence of a base and a solvent using, as alkylating agent, a dialkyl sulfate whose alkyl groups contain at least 6 carbon atoms, the molar ratio of saccharides to dialkyl sulfate being from 1:1 to 1:5. The reaction mixture obtainable in this way is used as a surfactant, preferably in detergents and cleaning agents.

The reaction of reducing saccharides with dialkyl sulfates proceeds according to the following reaction scheme:

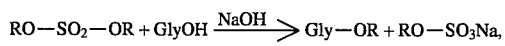

where GlyOH is a reducing saccharide and R is alkyl.

As long as the reducing saccharides and the dialkyl sulfate are used in a molar ratio of 1:1, practically equivalent amounts of alkyl monoglycosides and salts of alcohol sulfates are obtained. In the reaction of a dialkyl sulfate with reducing saccharide units, essentially only one alkyl group of the dialkyl sulfate reacts. After the alcohol sulfate has been neutralized by means of a base, preferably sodium hydroxide, an anionic surfactant is obtained if the dialkyl sulfate has at least 6 carbon atoms in the alkyl group. The resultant mixture may therefore be used instead of a conventional surfactant in detergents and cleaning agents. If on the other hand it is desired to prepare pure alkyl monoglycosides that are principally used as surfactants or emulsifiers, the reaction mixture formed in the above reaction of a dialkyl sulfate with reducing saccharide units has to be purified.

The dialkyl sulfate having at least 6 carbon atoms in the alkyl groups can readily be prepared from the corresponding alcohols having the same number of carbon atoms and for example sulfuryl chloride. The dialkyl sulfates that can be used may be characterized for example by means of the formula below

where R and R$^1$ may be identical or different and are C$_6$- to C$_{30}$-alkyl or C$_6$- to C$_{30}$-alkenyl. Of particular industrial interest are those compounds of the formula I in which R and R$^1$ are C$_6$- to C$_{30}$-alkyl, preferably C$_8$- to C$_{18}$-alkyl, or alkenyl.

In the above formula I, R and R$^1$ may in principle have different carbon chain lengths. When these dialkyl sulfates are used mixtures of two alkyl glycosides and mixtures of two alcohol sulfates are then obtained in the reaction. In the above formula I R is preferably identical to R$^1$.

The aliphatic alcohols that are used to prepare the dialkyl sulfates may be of any desired chain length, ie. with chain lengths of 6 to about 30 carbon atoms. In order to obtain surface-active reaction products that can be used as surfactant raw materials in detergents and cleaning agents, aliphatic primary alcohols having 6 to 20 carbon atoms, in particular having 8 to 18 carbon atoms, are preferred. These higher aliphatic alcohols are preferably prepared from industrial fats. However, it is of course also possible to use synthetic primary alcohols, for example oxo-alcohols, to prepare the dialkyl sulfates. The alkyl groups of the preferred dialkyl sulfates contain 6 to 30 carbon atoms and may have a double bond.

The higher aliphatic primary C$_{12}$- to C$_{18}$-alcohols which are particularly important as the alcohol component in the preparation of the dialkyl sulfates are preferably saturated and in particular straight-chain alcohols, such as can be obtained on an industrial scale by hydrogenation of natural fatty acids, for example the compounds n-dodecyl alcohol, n-tetradecyl alcohol, n-hexadecyl alcohol, n-octadecyl alcohol, n-octyl alcohol, n-decyl alcohol, undecyl alcohol and tridecyl alcohol. Since the fatty alcohols are preferably derived from natural fat sources, mixtures of industrial fatty alcohols may normally also be considered as suitable reactants. In addition to the actual fatty alcohols, branched-chain primary alcohols, for example oxo alcohols, are also suitable for the reaction. Typical oxo alcohols are for example $C_{12}$-$C_{13}$-alkanols with approximately 25% of mainly 2-methyl branching (Dobanol 23) and the corresponding $C_9$-$C_{11}$-alkanols (Dobanol 91).

The reducing saccharides may be monosaccharides, disaccharides or oligosaccharides or mixtures thereof, and are composed of conventional penroses and hexoses, such as aldopentoses, for example ribose, arabinose, xylose and lyxose, aldohexoses, for example allose, altrose, glucose, mannose, gulose, idose, galactose and talose, and ketohexoses, for example fructose. Mannose, glucose, galactose and fructose are preferred, and glucose is particularly preferred.

Disaccharides that may be used are in particular sucrose, lactose, maltose and cellobiose. In addition the sugar component may be used in the anhydrous form, or as monohydrate or syrup. In the latter case, the water content of the saccharide solutions may be from 10 to 80% by weight. Industrial dextrose syrups having a water content of from 20 to 40% by weight are preferred.

The reaction of a dialkyl sulfate with the reducing saccharides is carried out in the presence of a base. The base deprotonates the hydroxyl group in the C-1 position of the monosaccharide unit. The base is used in at least an equimolar ratio. The molar ratio of base to monosaccharide is 1:1 to 10:1, preferably 1:1 to 5:1. In most cases the molar ratio of the employed base to the monosaccharide is 1:1 to 2:1. The bases are hydroxides, amides, hydrides, oxides or carbonates of alkali metals and/or alkaline earth metals, boron hydride, sodium borohydride or hydrides, hydroxides, oxides or carbonates of aluminum. Preferred bases are sodium hydroxide, potassium hydroxide, sodium hydride, boron hydride, sodium borohydride, lithium hydride and lithium aluminum hydride. The corresponding salts of monoalkyl sulfates are formed according to the above reaction scheme by the addition of the base.

The molar ratio of saccharides to dialkyl sulfate is 1:1 to 1:5. If the mixture of alkyl monoglycoside and alcohol sulfate formed in the reaction is to be used directly as an additive to detergents and cleaning agents, it is recommended to use only a small excess of dialkyl sulfate in the preparation of the products, in which case the molar ratio of saccharide to dialkyl sulfate is for example 1:1 to 1:1.05. In this case water is preferably used as solvent, and sodium hydroxide or potassium hydroxide is preferably used as base. In principle other solvents may also be used, but it must be possible to separate them from the reaction products by distillation or chromatography. Compared with the other solvents water has the advantage that it can remain in the product. In order to control the reaction the molar ratio of alkyl monoglycosides to alcohol sulfate may be varied in the range from 3:2 to 2:3. In particular, mixtures of $C_6$- to $C_{30}$-alkyl monoglycosides and $C_6$- to $C_{30}$-alcohol sulfates are used in a molar ratio of 3:2 to 2:3 as surfactants in detergents and cleaning agents.

Water is the preferred solvent in the reaction of reducing saccharides with a dialkyl sulfate. Polar aprotic solvents and polar protic solvents are also suitable, for example hexamethylphosphoric triamide, dimethylformamide, N-methylpyrrolidone, dimethylpropyleneurea, dimethylethyleneurea, dimethoxyethane, tetrahydrofuran, dioxane and carbon dioxide. In many cases it may be advantageous to use mixtures of solvents. The amount of solvent used is generally not critical, and is usually from 20 to 90%, preferably 30 to 70% by weight, based on the reducing saccharides and dialkyl sulfate employed. Since nonionic and anionic surfactants are preferably simultaneously used in detergents and cleaning agents, the anionic surfactants generally predominating, the reaction mixture obtained on reaction of reducing saccharides with a dialkyl sulfate can readily be incorporated into conventional detergent and cleaning agent formulations. The reaction mixture can be mixed without any difficulty with additional anionic surfactants to give stable formulations. Suitable additives for the reaction mixtures produced by the process according to the invention include aryl sulfates, alcohol ether sulfates and alcohol sulfates.

In particular dimethylpropyleneurea and sodium hydride have proven suitable for preparing pure alkyl glycosides with separation of the alcohol sulfates from the reaction mixture. In this case the procedure can be carried out at from 0° to 100° C., preferably at from 20° to 30° C. The solvent is removed by vacuum distillation, and the alkyl monoglycoside and alkyl sulfate are preferably separated by chromatography on reverse-phase columns (abbreviated to RP columns).

The reaction of a dialkyl sulfate with reducing saccharides may also be carried out in the presence of water or other solvents at from 0° to 100° C. The reaction mixtures, which contain alkyl monoglycosides and alcohols sulfates as essential constituents, are used as surfactants. The aforedescribed process enables pure, surface-active alkyl monoglycosides to be prepared without excessive amounts of undesired by-products and waste products (e.g. alcohols, solvents or higher alkylated saccharides) being formed. Compared with the known processes for preparing alkyl glycosides described at the beginning, the process according to the invention can be carried out at very low temperatures, with the result that the alkyl monoglycosides obtained are extremely pale-colored and do not have to undergo any additional purification, for example bleaching. Whereas mixtures of alkyl monoglycosides, oligoglycosides and polyglycosides are obtained in the industrial processes for preparing alkyl glycosides, alkyl monoglycosides are obtained in the process according to the invention.

EXAMPLES

Example 1

90 g (0.5 mol) of glucose were dissolved in 400 ml of absolute hexamethylphosphoric triamide at 20° to 30° C.; 20 g (0.75 mol) of sodium hydride were added in portions. When the evolution of hydrogen was complete, 284 g (0.75 mol) of didecyl sulfate were added and the reaction mixture was stirred for 15 hours at 20° to 25° C. Excess sodium hydride was destroyed by means of methanol, and the solvent was removed under a high vacuum (0.05 mbar) at 110° C. The residue was taken up in 100 ml of water/methanol (3:7 parts by weight) and chromatographed on an $RP_{18}$ flash column. 99.2 g of decyl glucoside (62.5% yield) with an alpha/beta isomer ratio of 1:2 were obtained as an analytically pure product.

Example 2

135 g (0.75 mol) of galactose and 425 g (1.125 mol) of didecyl sulfate were suspended in 500 ml of dimethylpropyleneurea, the starting compounds partially dissolving. 28 g (1,125 mol) of sodium hydride were added at 20° to 30° C. and the reaction mixture was stirred for 18 hours. The excess sodium hydride was destroyed by means of methanol and the pale yellow solution was freed from solvent in a high vacuum (0.05 mbar) at 100° C. 198 g of decyl-alpha-D- galactopyranoside (83% yield) were obtained after workup by a method similar to that described in Example 1.

Example 3

Using glucose, 179 g of decyl glucoside (74% yield) with an alpha/beta isomer ratio of 1:3 is obtained in a manner similar to that of Example 2.

We claim:

1. A process for preparing alkyl glycosides comprising the step of:

alkylating reducing saccharides in the presence of a base and a solvent, with an alkylating agent, wherein said alkylating agent is a dialkyl sulfate whose alkyl groups contain at least six carbon atoms, and the molar ratio of said saccharides to said dialkyl sulfate being from 1:1 to 1:5.

2. A process as claimed in claim 1, wherein the alkyl groups of the dialkyl sulfate contain 6 to 30 carbon atoms and zero or one double bond.

3. A process as claimed in claim 1, wherein the molar ratio of the base to the saccharide units is 1:1 to 10:1.

4. A process as claimed in claim 1, wherein the base is selected from the group consisting of hydroxides, hydrides, oxides and carbonates of alkali metals, alkaline earth metals, mixed alkali-alkaline earth metal, and aluminum; boron hydride; sodium borohydride; and alkali metal, alkaline earth metal and mixed alkali-alkaline earth metal amides.

5. A process as claimed in claim 1, wherein the alkyl groups of the dialkyl sulfate contain 8 to 18 carbon atoms and zero or one double bond.

6. A process as claimed in claim 1, wherein both alkyl groups of the dialkyl sulfate are identical.

7. A process as claimed in claim 1, wherein said reducing saccharides are monosaccharides, disaccharides, olgasaccharides or mixtures thereof.

8. A process as claimed in claim 1, wherein said reducing saccharides are composed of aldopentoses, aldohexoses or ketohexoses.

9. A process as claimed in claim 8, wherein said reducing saccharides are composed of members selected from the group consisting of ribose, arabinose, xylose, lyxose, allose, altrose, glucose, mannose, gulose, idose, galactose, talose and fructose.

10. A process as claimed in claim 8, wherein said reducing saccharides are composed of a saccharide selected from the group consisting of mannose, glucose, galactose and fructose.

11. A process as claimed in claim 1, wherein said reducing saccharide is selected from the group consisting of sucrose, lactose, maltose and cellobios.

12. A process as claimed in claim 1, wherein the molar ratio of saccharide to dialkyl sulfate is from 1:1 to 1:1.05.

13. A process as claimed in claim 1, wherein said solvent is water.

14. A process as claimed in claim 1, wherein said base is sodium hydroxide or potassium hydroxide.

15. A process as claimed in claim 1, wherein said solvent is a polar solvent selected from the group consisting of hexamethylphosphoric triamide, dimethylformamide, N-methylpyrrolidone, dimethylpropyleneurea, dimethylethyleneurea, dimethoxyethane, tetrahydrofuran, dioxane, carbon dioxide and mixtures thereof.

16. A process as claimed in claim 1, wherein said solvent is dimethylpropyleneurea and said base is sodium hydride.

* * * * *